United States Patent
Pape (10) Patent No.: US 10,650,691 B2
(45) Date of Patent: May 12, 2020

(54) MOBILITY AID

(71) Applicant: Lise S Pape, London (GB)

(72) Inventor: Lise S Pape, London (GB)

(*) Notice: Subject to any disclaimer, the term of this patent is extended or adjusted under 35 U.S.C. 154(b) by 466 days.

(21) Appl. No.: 15/316,955

(22) PCT Filed: Jun. 12, 2015

(86) PCT No.: PCT/GB2015/051730
§ 371 (c)(1),
(2) Date: Dec. 7, 2016

(87) PCT Pub. No.: WO2015/189631
PCT Pub. Date: Dec. 17, 2015

(65) Prior Publication Data
US 2017/0116869 A1 Apr. 27, 2017

(30) Foreign Application Priority Data

Jun. 14, 2014 (GB) .................................. 1410648.8
Feb. 13, 2015 (GB) .................................. 1502368.2

(51) Int. Cl.
*G09B 19/00* (2006.01)
*G09B 5/02* (2006.01)
*A61H 1/02* (2006.01)

(52) U.S. Cl.
CPC ............ *G09B 5/02* (2013.01); *A61H 1/0262* (2013.01); *G09B 19/003* (2013.01); *A61H 2201/5064* (2013.01); *A61H 2201/5071* (2013.01)

(58) Field of Classification Search
None
See application file for complete search history.

(56) References Cited

U.S. PATENT DOCUMENTS

| | | |
|---|---|---|
| 5,357,696 A | 10/1994 | Gray et al. |
| 5,575,294 A | 11/1996 | Perry et al. |
| 5,738,432 A | 4/1998 | Okko et al. |
| 6,033,370 A | 3/2000 | Reinbold et al. |
| 6,122,846 A | 9/2000 | Gray |
| 6,273,863 B1 | 8/2001 | Avni et al. |

(Continued)

FOREIGN PATENT DOCUMENTS

| | | |
|---|---|---|
| CN | 104287945 A | 1/2015 |
| DE | 29711438 U1 | 2/1998 |

(Continued)

OTHER PUBLICATIONS

International Search Report for Appl No. PCT/GB2015/051730 dated Aug. 6, 2015, 6 pages.

(Continued)

*Primary Examiner* — Bruk A Gebremichael
(74) *Attorney, Agent, or Firm* — Haley Guiliano LLP (57) ABSTRACT

The present invention provides a system (10, 110) for aiding a user to move, comprising: a sensor (20,120) configured to detect a parameter indicating a position of the user's foot; a feedback device (30, 130) operable to provide feedback to the user; and a processor, wherein the processor is configured to control the feedback device (30,130) depending on the sensed parameter. The present invention is beneficial because it increases confidence and/or efficiency in movement, providing visual aids and/or tactile feedback to guide the user.

3 Claims, 11 Drawing Sheets

(56) References Cited

U.S. PATENT DOCUMENTS

| | | |
|---|---|---|
| 6,978,684 B2 | 12/2005 | Nurse |
| 2003/0184441 A1 | 10/2003 | Nanayakkara |
| 2004/0173220 A1* | 9/2004 | Harry ................... A43B 3/0005 128/892 |
| 2005/0239567 A1* | 10/2005 | Elliott .................. A43B 1/0036 473/207 |
| 2006/0025836 A1 | 2/2006 | Van Gerpen et al. |
| 2007/0130803 A1* | 6/2007 | Levy .................... A43B 1/0027 36/136 |
| 2007/0204687 A1 | 9/2007 | Haselhurst |
| 2010/0146822 A1* | 6/2010 | MacGregor .......... A43B 3/0005 36/136 |
| 2012/0119920 A1 | 5/2012 | Sallop et al. |
| 2013/0069862 A1 | 3/2013 | Ur |
| 2013/0218052 A1 | 8/2013 | Blair, III |
| 2014/0118498 A1 | 5/2014 | Lee et al. |
| 2014/0243710 A1* | 8/2014 | Jeong ................... A61B 5/1116 600/594 |

FOREIGN PATENT DOCUMENTS

| | | |
|---|---|---|
| DE | 202009018402 U | 12/2011 |
| GB | 2489406 A | 10/2012 |
| JP | 2004073436 | 3/2004 |
| KR | 20130101861 A | 9/2013 |
| NL | 1036637 C | 8/2010 |
| WO | 2011130223 A1 | 10/2011 |
| WO | 2014107754 A2 | 7/2014 |
| WO | 20140141291 A2 | 9/2014 |

OTHER PUBLICATIONS

International Preliminary Report on Patentability for Appl No. PCT/GB2015/051730 dated Dec. 15, 2016, 8 pages.

Great Britain Combined Search and Examination Report for Appl No. GB1502368.2 dated Apr. 17, 2015, 3 pages.

Great Britain Further Search Report for Appl No. GB1502368.2 dated Oct. 22, 2015, 2 pages.

Great Britain Examination Report for Appl No. GB1502368.2 dated Jul. 13, 2016, 4 pages.

Great Britain Search & Exam Report for Appl No. GB1614148.3 dated Sep. 9, 2016, 6 pages.

Great Britain Examination Report for Appl No. GB1614148.3 dated Dec. 15, 2016, 3 pages.

Zhao et al conference proceedings of 35th annual international conference of the IEEE EMBS, Osaka, Japan, Jul. 3-7, 2013; p. 5895-5898.

EP Extended Search Report of EP 18203437.1 dated Feb. 15, 2019.

* cited by examiner

MOBILITY AID

RELATED APPLICATIONS

This application is a national phase application filed under 35 USC § 371 of PCT Application No. PCT/GB2015/051730 with an international filing date of Jun. 12, 2015, which claims priority to GB1410648.8, filed Jun. 14, 2014 and GB1502368.2, filed Feb. 13, 2015. Each of these applications is herein incorporated by reference in their entirety for all purposes.

FILED OF THE INVENTION

THE PRESENT INVENTION relates to a mobility aid and more particularly to an aid that provides visual cues and/or tactile feedback for a user.

INTRODUCTION

The present invention relates to a mobility aid to assist in the everyday life of a person with mobility issues. Posture and balance for walking in particular are intricately linked to proprioception, the ability to sense the position, location, orientation and movement of the body and its parts. Proprioception and other sensory feedback is often impaired in patients with diseases such as multiple sclerosis (MS) and Parkinson's disease (PD) for example. These diseases often result uneven walking.

For example, in normal gait, the heel strikes the ground before the toes (heel-to-toe walking). In Parkinsonian gait, the entire foot is often placed on the ground at the same time, or the toes touch the ground before the heel. In addition, PD patients may have reduced foot lifting clearance between the toes and the ground. Postural instability increases the likelihood of a patient falling, the consequences of which are obvious.

This invention is also helpful for other persons with lessened sensory feedback. It can also be helpful in sports for people with no mobility issues, but who wish to receive active feedback on their posture or gait, to review and revise their posture/gait e.g. when running. The device may also be helpful for anyone during general walking, to predict and detect changes in walking.

The present invention aims to provide a mobility aid to enhance a user's ability to move stably and/or efficiently. The invention can also reduce the risk of the user falling.

BRIEF SUMMARY OF THE INVENTION

The present invention provides a system and method for aiding a user as claimed.

In particular, the present invention provides a system for aiding a user to move, comprising: a sensor configured to detect a parameter indicating a position of the user's foot; a feedback device operable to provide feedback to the user; and a processor, wherein the processor is configured to control the feedback device depending on the sensed parameter.

Preferably, the present invention provides a system for aiding a user to move, comprising: a sensor configured to detect a parameter indicating a position of the user's foot; a projector operable to project a first visual cue; and a processor, wherein the processor is configured to control the projector depending on the sensed parameter.

Preferably, the present invention provides a system for aiding a user to move, comprising: a sensor configured to detect a parameter indicating a position of the user's foot; a motor operable to provide vibrational feedback in response to the sensor output; and a processor, wherein the processor is configured to control the vibrational feedback depending on the sensed parameter.

The present invention is beneficial because it increases confidence and/or efficiency in movement—it provides visual aids and/or tactile feedback to guide the user. It also promotes independence. Further, the invention is environmentally-friendly, because it promotes travel by walking.

Embodiments of the present invention will now be described, by way of example only, with reference to the following figures, in which.

DETAILED DESCRIPTION OF THE INVENTION

Figure 1:
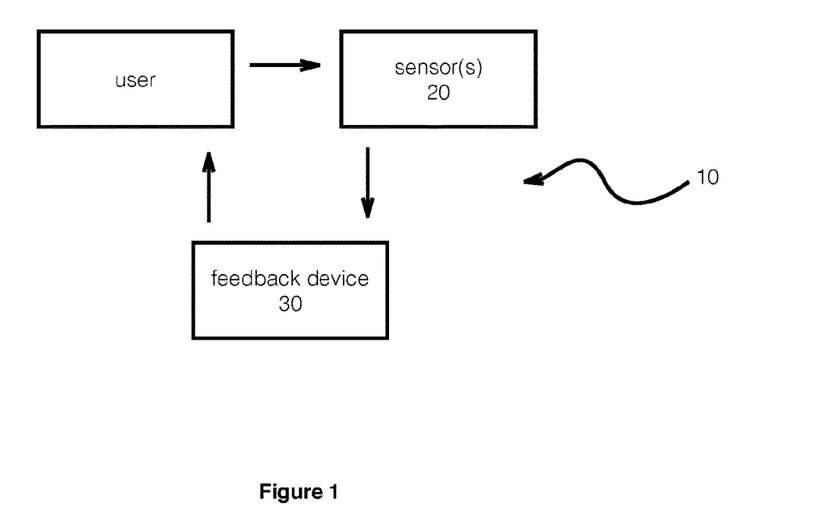
FIGS. 1 and 2 show schematic overviews of the present invention.

The present invention is illustrated in FIG. 1, which shows the core elements of the system 10: a sensor 20 for sensing a parameter indicating a position of the user's foot and a feedback device 30 to provide feedback to enhance proprioception and sensory feedback.

In a first embodiment, the feedback device 30 is a projector in the form of a laser, and the laser provides one or more visual cues in response to the sensed parameter, to aid the user in walking. In the first embodiment, the sensor 20 is a pressure sensor, detecting the pressure exerted by the user on a surface such as the ground. In other embodiments, a distance sensor is used.

In use, the pressure sensor 20 measures the contact pressure between the user's foot and the walking surface. When the user's foot touches the surface and the sensed pressure exceeds a threshold, a line projection is emitted by the laser, indicating a path for the user to travel along. When the sensed pressure falls below the threshold, the laser is switched off, to preserve battery life.

Figure 3:
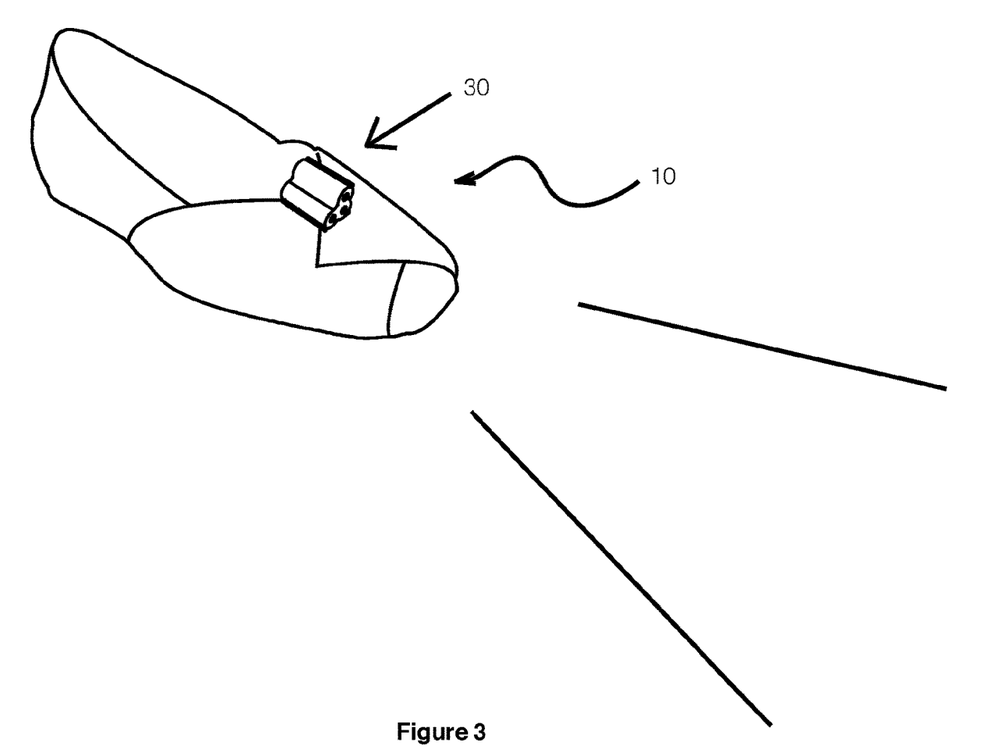
FIG. 3 shows a shoe comprising an attachment illustrating a first embodiment of the present invention.
Figure 4:
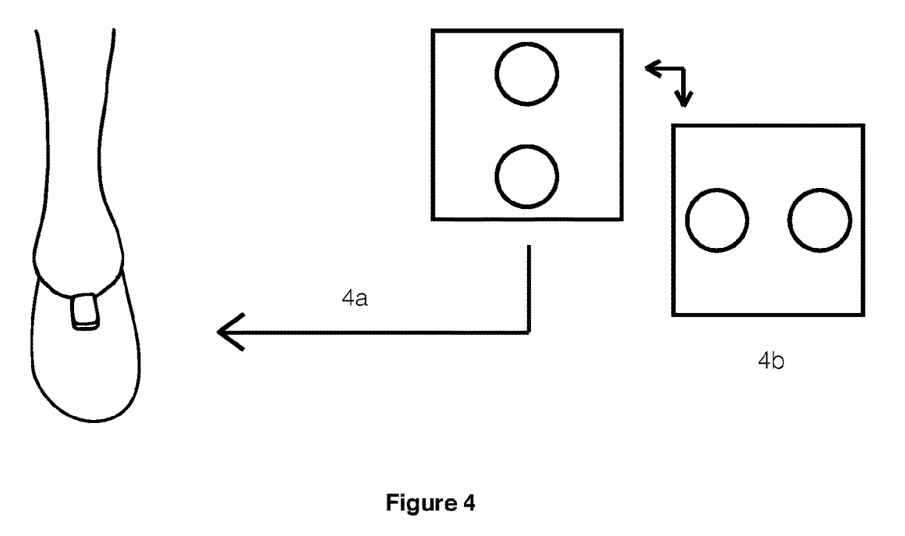
FIGS. 4 and 5 show the embodiment of FIG. 3 in more detail.
Figure 5:
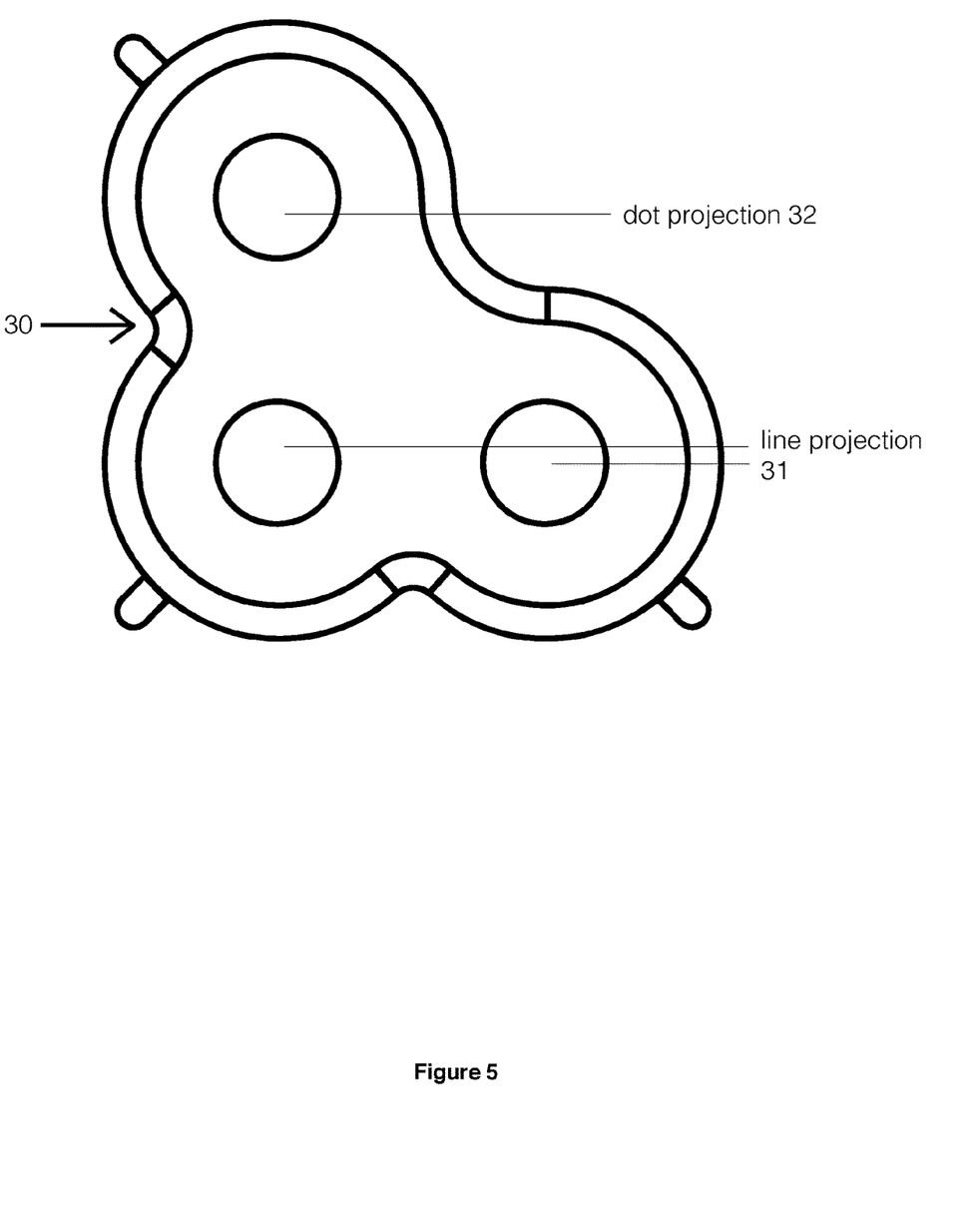

A preferred implementation of the laser line projection is illustrated in FIGS. 3-5. In these figures, the laser projector 30 comprises three laser elements: two lower line projection laser elements 31 and an upper dot projection element 32. The two lower laser elements are arranged to project at an angle of substantially 45-60° to provide a suitable diverging walking path. The dot projection is focused above the line projections, so that it reflects off obstacles in the user's path.

In the preferred arrangement shown, the two laser elements 31 are placed at the front of the shoe. This is a preferred location for the laser elements 31 because it is the last area to move out of contact with the ground surface during the gait cycle. The angle of the projection varies according to the individual user. The angle of the projection determines the projection distance from the shoe and is influenced by the gait stride and size of the user. This is discussed further with reference to FIG. 11 below.

In other embodiments, the laser projection may comprise a different number of laser elements 31—for example one laser element 31 may be configured to provide both the line and dot projections, switching between the two.

In preferred embodiments, the visual cues comprise two elements: line and dot projections. The line projections provide a path for the user to follow. In terms of overcoming fear of falling and promoting movement, there are different needs for different users. MS patients will have a need for the path (line) projection, whereas PD users suffering from FOG (freezing of gait) need obstruction identification/projection. For both types of users, the dot projection is a guideline for avoiding obstacles. Preferably, the dot projection (obstacle identification) is presented when a foot is not touching the surface and the sensed pressure is below a threshold. In some embodiments, the thresholds for the dot and line projections are the same, so the system switches between line and dot projections as the user walks. In other embodiments, the thresholds are not the same, and may overlap. In other embodiments, the dot and/or line projections may also be "on", regardless of any thresholds.

Preferably, the dot projection has a diameter and brightness that makes it easily visible for the user to identify obstacles. These dot projection parameters can be determined by the particular objects that the user finds difficulty in avoiding, e.g. steps. Since steps are to be avoided at a short distance, the required diameter of the projection may be relatively small, e.g. at least 3 mm at 0.2 m or less from the step obstacle. For obstacles that need to be avoided early, e.g. bins or lamp posts that must be walked around, the same diameter may be required at a distance of 0.5 m or less, and these parameters would still be suitable for steps (but increase power consumption).

In other embodiments, such as sports training, other types of projection may be required to e.g. advise the user on the best steps to pursue in order to enhance performance. Preferably, these parameters can be configured by the user.

In some embodiments, the system further comprises a distance or proximity sensor for detecting the distance to/presence of obstacles, and the system is configured to provide a visual cue such as a dot projection to highlight the obstacle, in response to the sensor feedback. Accordingly, the dot projection parameters may be configured by the system automatically, using the sensor information. The system may optionally provide additional audible, vibrational or visual feedback when the obstacle is within a predetermined proximity/distance.

Figure 2:
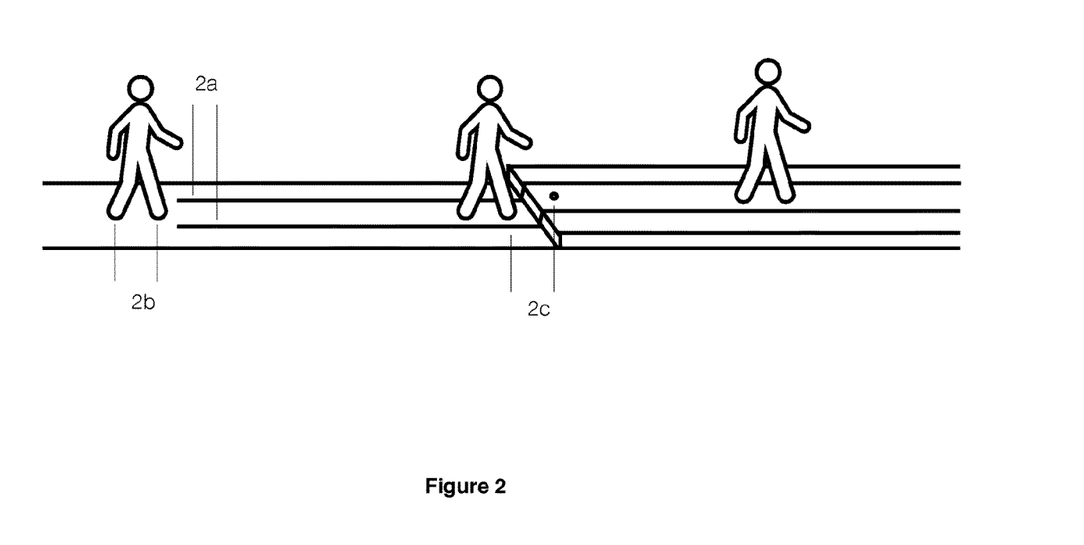

The combined path and obstacle identification system is illustrated schematically in FIG. 2. Here, the shoe clip is attached on the front of the user's shoe, as shown in FIG. 3, where a path is projected from the right shoe of the wearer. This guidance path helps when moving the left foot that is currently travelling. Once the left foot is on the ground, it will similarly project a path for the right foot to follow. The shoe clip is preferably connected to the insole via a wireless connection such as Bluetooth® but it may also be hard wired. The insole informs the activity in terms of laser projection from the shoe clip (FIG. 2, step 2*a*), where a guidance pathway is projected from the user via 'Path Finder'. As the user approaches an obstacle, the visual stimuli will help to alert the user whether it is safe to pass (FIG. 2, step 2*c*). Pressure observed in the insole is used to determine which laser is on at which time, as explained further below, and tactile feedback may optionally be given for each step indicating surface hardness through 'Path Feel' (FIG. 2, step 2*b*). The programming of events can be changed and customised for different scenarios. For instance, the need in healthcare may be different to the need in sports scenarios.

In some embodiments, the laser component can be turned 90 degrees, to project vertically (4*a*) and/or horizontally (4*b*). This 90° rotation is illustrated in FIGS. 4 and 5, where the laser element is placed at the front of the shoe (FIGS. 4*a* and 4*b*). Alternatively, an optical diffractive element may be used. The different projections are used for the different needs of users. For example, an MS user may observe increased confidence when being supported by the visual path which acts as guidance. The PD user benefits from having obstruction projected; particularly patients suffering from FOG. The obstructions are visual cues that can help to trigger movement, when the user is otherwise in a 'frozen' state.

Figure 6:
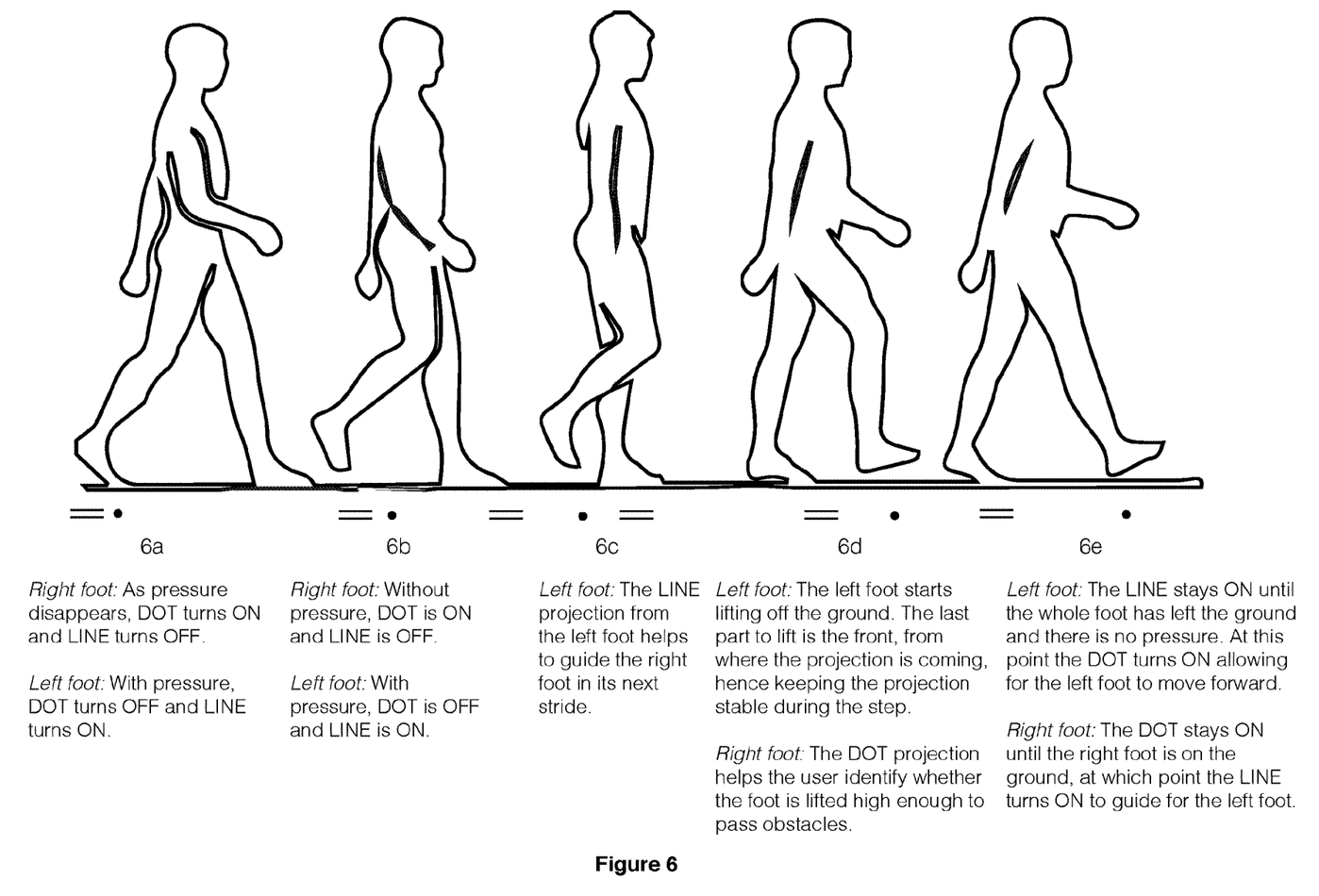
FIGS. 6 and 7 illustrate how two visual cue mechanisms operate in relation to a user's stride according to the first embodiment.
Figure 7:
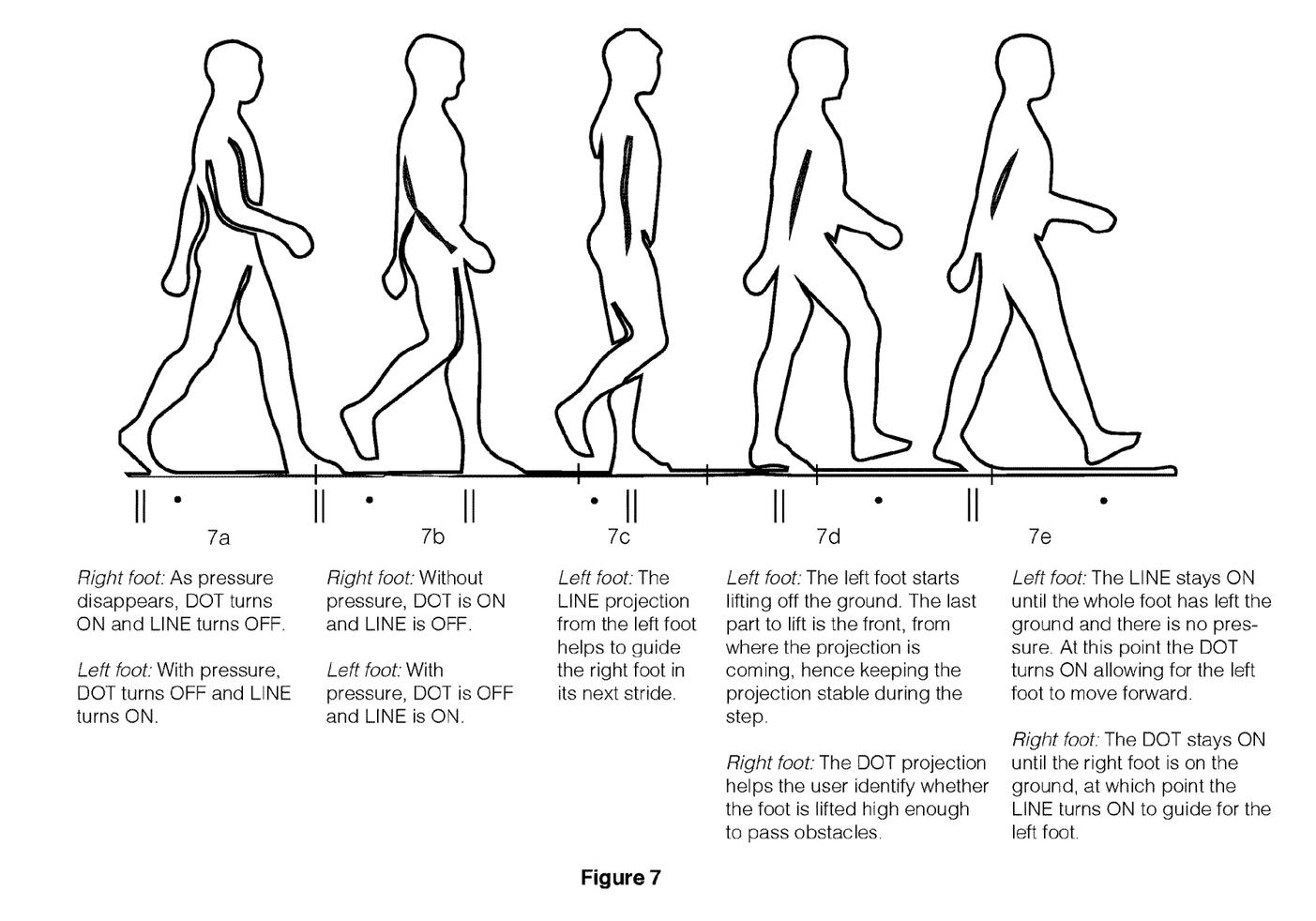

FIGS. 6 and 7 illustrate the interactions between the visual cues and the user's feet positions whilst walking. In summary, the line projection (path indication) is presented when the user's foot touches the surface and the sensed pressure exceeds a threshold. The dot projection (obstacle identification) is presented when a foot is not touching the surface and the sensed pressure is below a threshold. In this way, the feet act together in a coordinated fashion to support the movement of each other, e.g. the left foot projects for the right and vice versa. In FIG. 6, the projector is horizontal as FIG. 4*b* and the line projection is in the direction of the user's intended path. In FIG. 7, the line projection is 'vertical', as shown in FIG. 4*a*. The 'horizontal' projection projects a path for the user to follow and the 'vertical' projection projects a step interval e.g. in the form of two parallel, vertically spaced-apart lines for highlighting obstacles. In some embodiments, the vertical projection is paired with distance sensors to measure a distance to the obstacle(s), preferably providing an output in response to the sensed distance.

Figure 8:
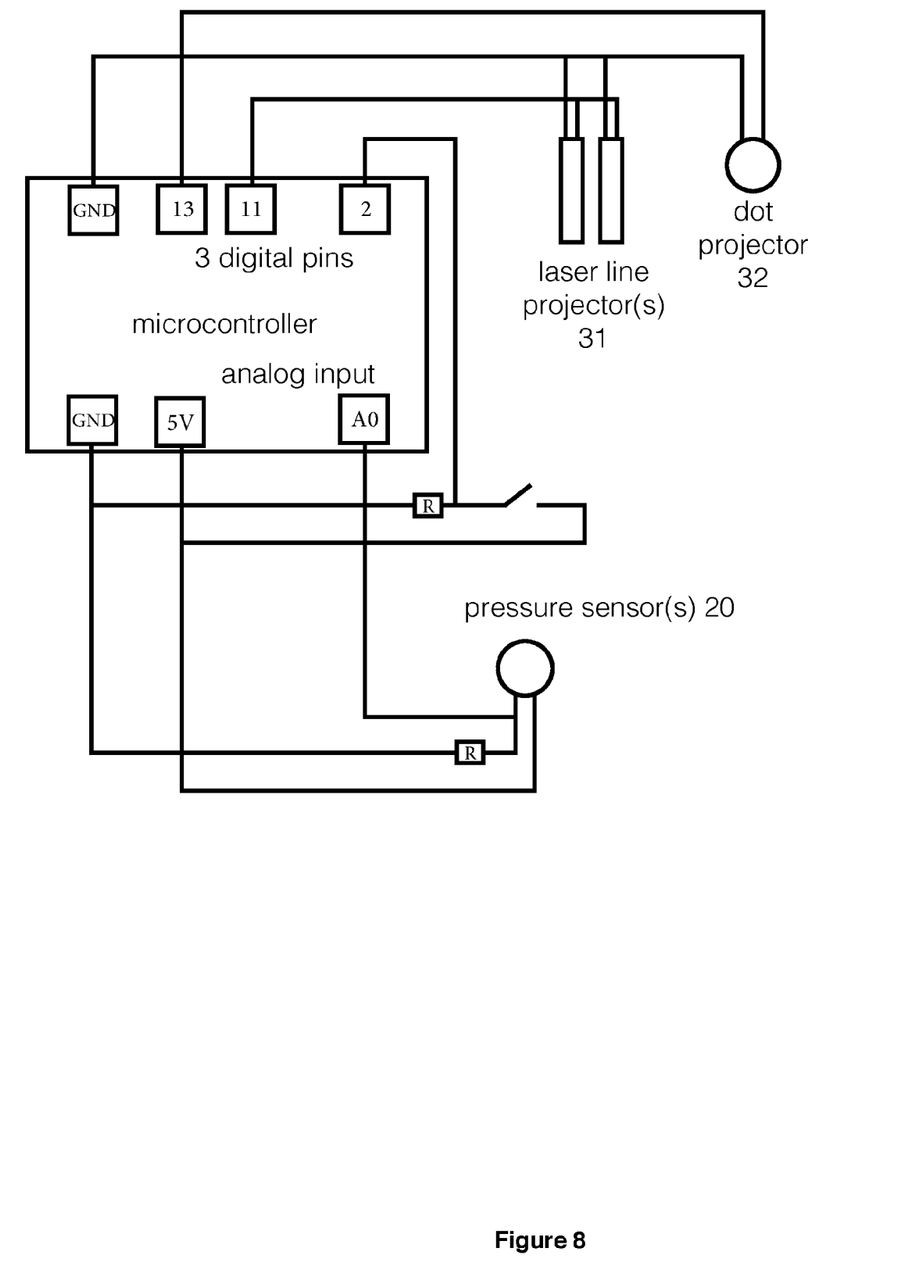
FIG. 8 illustrates an electronic layout for the first embodiment of the present invention.

FIG. 8 illustrates an electronic layout for the first embodiment of the present invention. The laser projections are influenced by the pressure coming from the insole (illustrated in FIGS. 6 and 7 and by the sensor placed in the electronic layout). The dot projection is ON when there is no pressure, and the foot is travelling, at which point the line projection is OFF on that foot. The opposite foot will have the reverse timing, and i.e. when the right foot is travelling, the left foot is on the ground, thereby activating pressure. When pressure is on, the laser line is ON and the dot projection is OFF. It is possible for the user to switch off the entire system using a main switch. The system is preferably also configured to turn off automatically after a given time when the pressure is substantially constant and it can be assumed that the user is standing still (constant high pressure) or seated (constant high, low or zero pressure, depending on the support of the feet).

Figure 9:
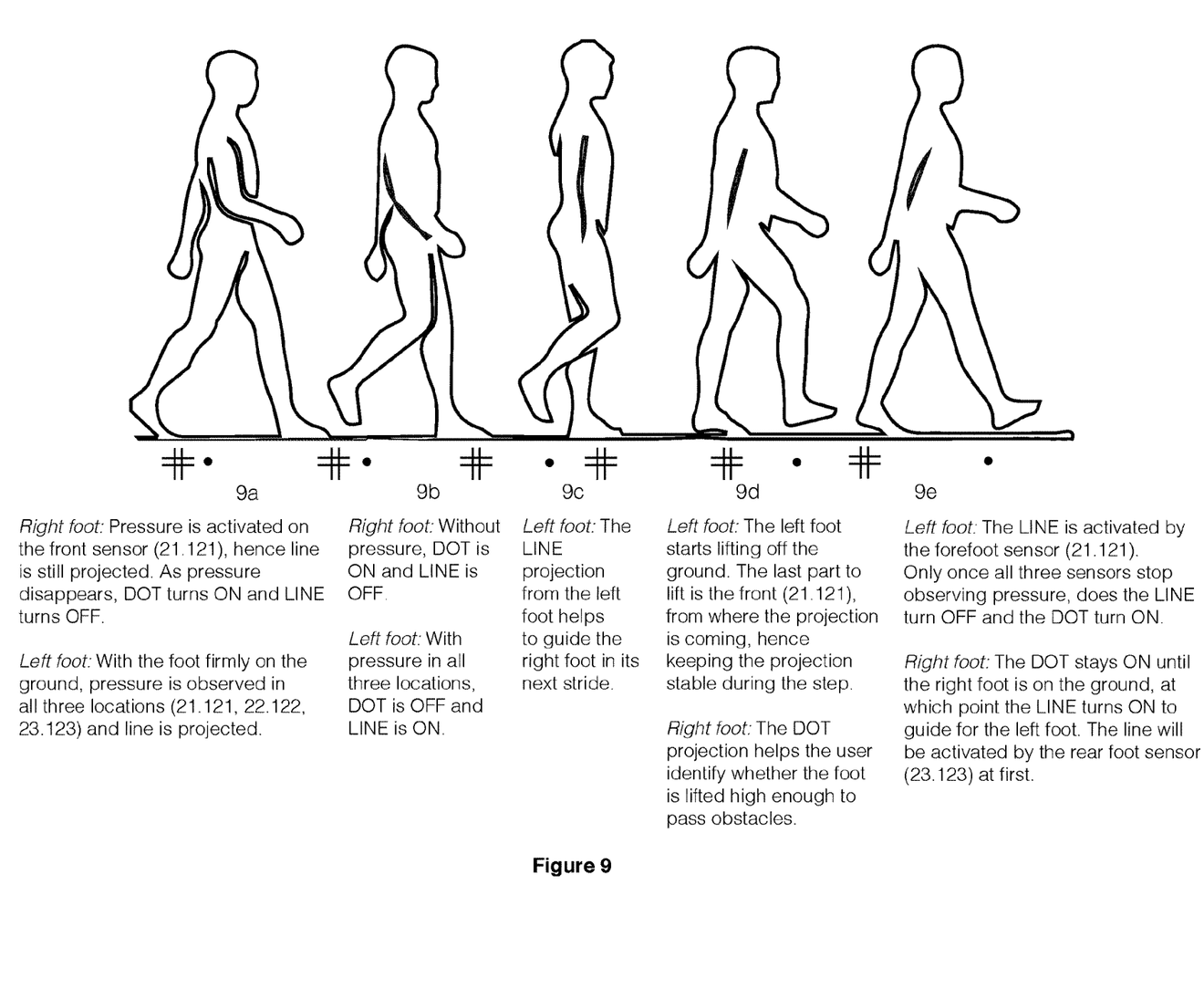
FIG. 9 illustrates how two different visual cue feedback mechanisms may operate in response to sensed pressure according to one embodiment.

FIG. 9 illustrates how the line and dot visual feedback mechanisms may operate in response to the sensed pressure. Here, there are three pressure sensors 20: forefoot 21, mid foot 22 and rear foot 23. In the illustrated embodiment, the line projection is enabled when any sensor detects pressure from the user's foot contacting the floor. The dot projection is enabled when none of the sensors detect a pressure indicating contact with the floor. In the illustration of FIG. 9, both 'horizontal' and 'vertical' line projections are shown. In embodiments, any combination of the line (horizontal and/or vertical) and/or dot projections may be used.

In some embodiments with multiple sensors 20, the threshold for the line projection is preferably linked to both the toe (or forefoot) sensor 21 and the heel (or rear-foot) sensors 23, since the heel sensor is the first to touch down and activate the line projection and the toe sensor is the last to leave the ground in the gait cycle. Accordingly, the line projection may be activated when the toe and/or heel sensors 21,23 sense a pressure exceeding the pressure threshold; and deactivated when both sensors sense a pressure below the threshold. For a distance sensor, the line projection may be activated when the toe and/or heel sensors sense a distance below the distance threshold; and deactivated when both sense a distance exceeding the threshold. The appropriate thresholding can similarly be applied for other sensors. Of course, some users may have different gait cycles and hence different needs, for instance if they suffer from foot-drop.

The threshold for the dot projection is also preferably linked to the toe and/or heel sensors for the same reason. Here, the functionality of the projector (both line and dot projections) is solely determined by the sensed parameter(s) of the elected threshold sensor(s)—the other sensors do not affect the switching of the projector. Depending on the user's gait, other sensors or combinations thereof may be the elected 'threshold' sensors.

In some embodiments, the sensors 20 work collectively and the sensed parameter is determined as an average or sum of the separate sensor outputs. In some embodiments, particular sensors may be weighted in the calculations. In some embodiments, only one of the line and dot projections is provided; in others, both are provided.

In the embodiments shown, three lasers are used to project two lines and one dot. The timing of each event is determined by the gait of the wearer. Other ways of projecting laser may include the use of fewer or more laser elements, e.g. one or two lasers.

For the line projection, a suitable force (or equivalent pressure) threshold for enabling the projection might be ≥45% or ≥50% of the user's weight detected by the sensor(s) on a single foot. When the detected force is substantially equal to the user's weight, this indicates that only that foot is touching the ground. When the detected force is substantially half the user's weight, this indicates that both feet are in contact with the ground, each supporting approximately 50% of the force (thus a 45% threshold provides a 10% margin of error or imbalance).

For the dot projection, a suitable force (pressure) threshold for enabling the dot might be 0% of the user's weight, or even substantially zero, so the foot is only lightly supporting the user, or not at all. In other embodiments, alternative thresholds are used, e.g. a single (substantially) zero threshold: if there is no pressure detected then the dot projection is enabled; and any non-zero pressure enables the line projection.

In a second embodiment, the present invention provides a feedback device in the form of a motor, wherein the motor provides vibratory feedback in response to the sensed parameter. In some embodiments, the motor is implemented within an insole of footwear.

The insole provides tactile feedback in order to give the user an increased somatosensory feedback and proprioceptive understanding and sensory feedback in general. The insole can be personalised to fit the feet of each user, and provide the required support and feedback, however, a generalised insole may be used in some applications. Each user may also have different levels of sensory perception depending on the level of impairment, hence different vibrational levels may be needed. These settings are preferably adjustable when the user initially calibrates the insole. The calibration may be completed using an app on a smartphone or similar.

In the second embodiment, the insole comprises a pressure sensor 120 and a vibration motor 130. The pressure sensor 120 detects changes in pressure and amount of pressure, allowing the vibration feedback to be directly (or inversely) correlated with the amount of pressure. Hence, different surfaces result in different amounts of vibration, the vibration varying in direct or inverse proportion to the pressure. It is therefore possible for a user to detect the hardness of a surface, as e.g. stepping in mud will give less strong vibrations than stepping onto a concrete surface (mode 1). With inverse correlation, stepping in mud will give stronger vibrations than stepping onto a concrete surface (mode 2). In other embodiments, the vibration level operates like a traffic light system having three tiers indicating the rigidity of the surface to the user, rather than proportional correlation, as tabulated below:

| Surface | Mode 1 | Mode 2 |
| --- | --- | --- |
| Concrete (stable, solid) | Strong vibration | Mild vibration |
| Mud (moderate) | Moderate vibration | Moderate vibration |
| Sponge (unstable) | Mild vibration | Strong vibration |

For other purposes, the vibration may be used to guide and train the wearer. In sports scenarios, it could be used for performance enhancement by vibrating when the wearer needs to run faster to improve their time over a given distance. It could also be used to correct running gait by measuring posture and providing corrective feedback accordingly.

Alternatively, multiple distance sensors could be used and the system can determine whether the distance from the underside of the foot to the surface at multiple locations, and thus whether the surface is flat or uneven. In some embodiments, pressure is observed in three locations, at the forefoot with sensor 121, mid foot with sensor 122 and rear foot with sensor 123. Vibrational feedback may optionally be provided in the same three locations with the respective forefoot motor 131, mid foot motor 132 and rear foot motor 133.

The increased proprioceptive and sensory feedback will come through the vibration motors 130 placed within the insole and activated by feedback from the pressure sensors 120. Additionally, the insole can be customised to the individual, providing touch on the entire sole of the foot, as opposed to what most people have today—a flat shoe, that only provides touch on the pressure points at the front and heel of the foot. In other embodiments, vibrators may be located remotely from the insole, e.g. on a wristband, to stimulate other parts of the user in use—particularly if the user is has a low touch sensitivity at their feet. In the case of amputees, there may also be other locations used to transfer the sense of touch from the feet or other body part.

Figure 10:
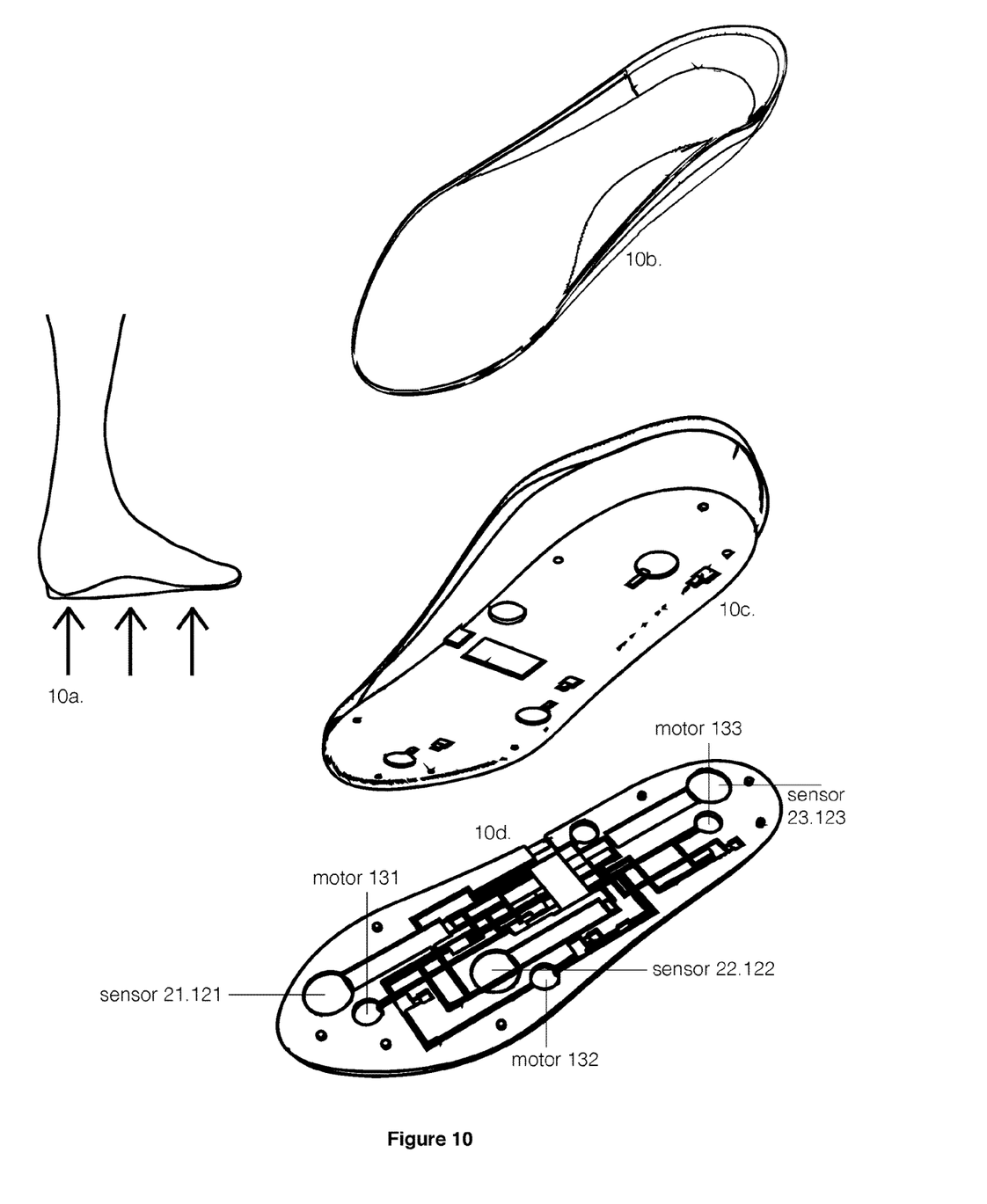
FIG. 10 illustrates an insole embodying the present invention.

Exemplary insoles and a moulded prototype are shown in FIG. 10. FIG. 10 shows four images: a) a visualization of the sensory feedback provided from the ground (via the insole) using haptics in the form of vibration; b) an upper view of the upper layer; c) a lower view of the upper layer; and d)

an upper view of the lower layer. The electronic parts sit between the upper and lower layers.

As shown in FIG. 10d, in this embodiment pressure is observed in three locations, at the forefoot with sensor 21,121, mid foot with sensor 22,122 and rear foot with sensor 23,123. Vibrational feedback may optionally be provided in the same three locations with the respective forefoot motor 131, mid foot motor 132 and rear foot motor 133.

Figure 11:
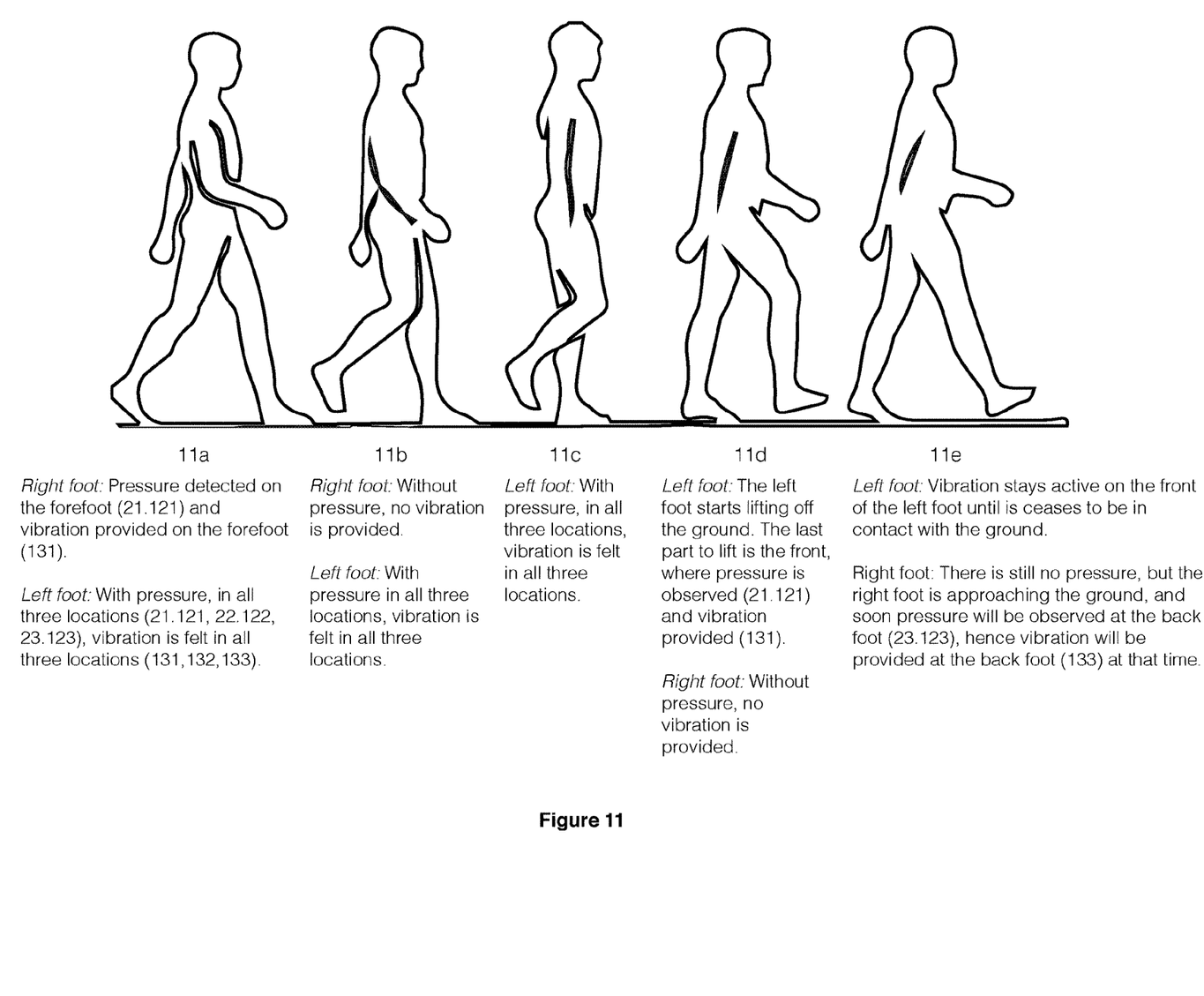
FIG. 11 illustrates how a vibrational feedback mechanism embodying the invention may operate in response to sensed pressure.

A schematic of the vibrational activation is shown in FIG. 11. In this embodiment, when there is no pressure, there is no vibration. Here, as the pressure increases, the vibrational feedback increases. As specified above, the pressure-feedback can be supplied in a number of ways depending on the use and the requirements from the user. In the embodiment described in FIG. 11, the vibrational feedback is provided in direct proportion to the pressure observed. In other embodiments, the feedback may be used in other ways, such as to influence running gait or to enhance performance as a training device. It may also be used to correct posture, in which case the haptic feedback may again be used differently.

Figure 12:
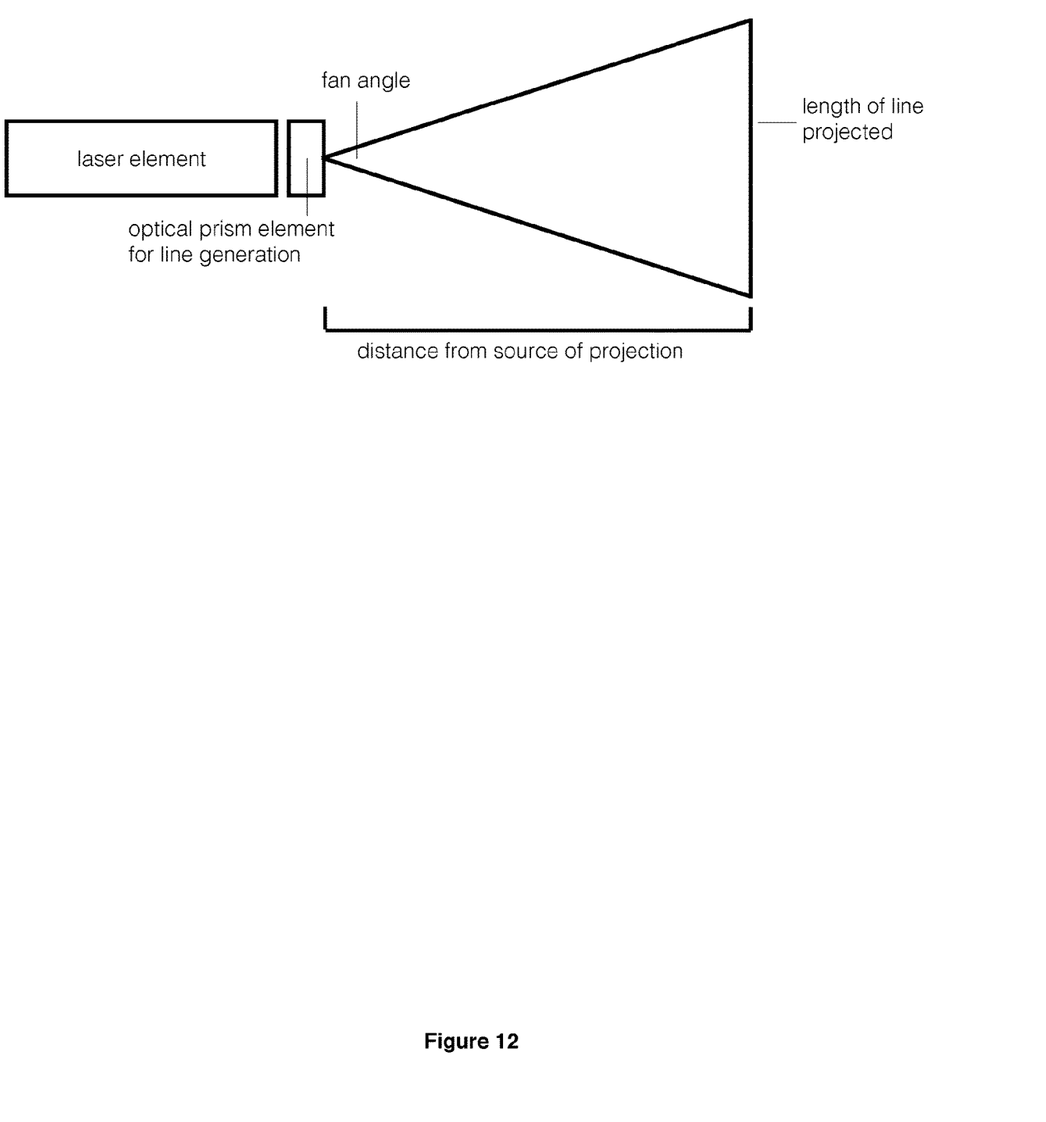
FIG. 12 illustrates a method for determining the optimal angle of projection.

FIG. 12 illustrates the placement of the optical element for the line projection. For the creation of a dot projection, no optical element is necessary. The optimal projector location is the top of the forefoot, as this is the last place to move during the gait cycle. It is therefore a stable place from which to project. The angle of the projection element used is determined by the user's gait and needs.

For instance, in order to project at a distance of 500 mm from the source (the shoe of the wearer), a fan angle of 45 degrees will provide a line which is approximately 410 mm in length. Should the desired projection distance from source be 400 mm, a fan angle of about 55 degrees provides a line of the same length as in the previous example. These figures are calculated from manufacturer's data, available online at http://www.global-lasertech.co.uk/line-fan-angle-calculator/.

Figure 13:
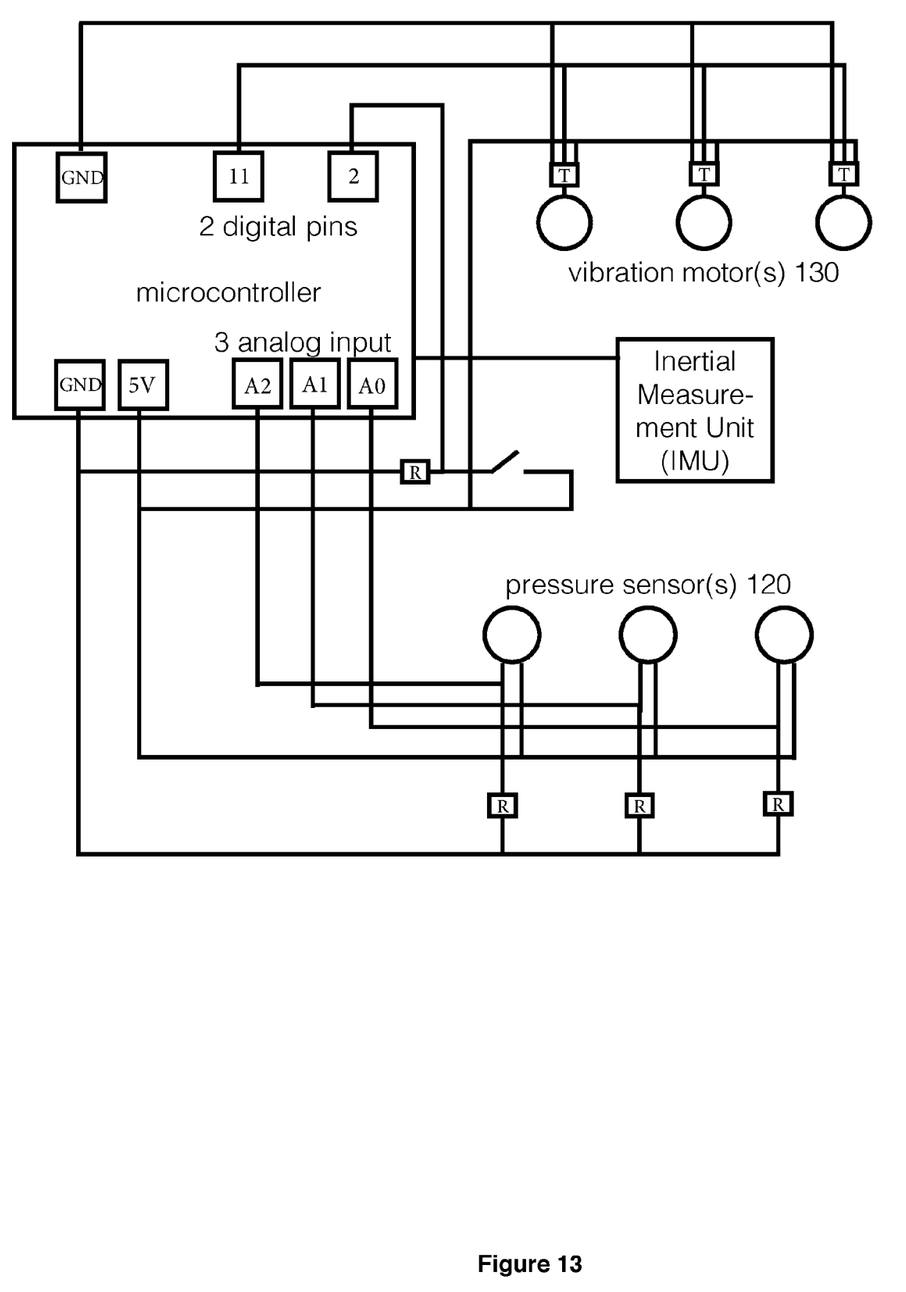
FIG. 13 illustrates an electronic layout for the vibrational feedback mechanism of FIGS. 10 and 11.

FIG. 13 illustrates an electronic layout for the second embodiment of the present invention. The vibration motor(s) are activated by the pressure sensor(s) as discussed above. An Inertial Measurement Unit may be included in some embodiments to provide information about balance, velocity, orientation and gravitational forces, and being able to derive further information about the wearer's gait. Combining IMU sensor data with pressure sensor data enhances the accuracy of the foot position monitoring capability.

In the first embodiment, the pressure sensor 20 is used to detect the position of the user's foot, which may be determined as a binary contact status: in contact with a surface, or not in contact with a surface. In other embodiments, the position is detected to a degree using a pressure sensor 120 or distance sensor.

The preferred embodiments use a pressure sensor 20, 120 to measure a pressure exerted by the user on a surface. In other embodiments, any other sensor may be used, such as a proximity sensor, a light sensor or a distance sensor (e.g. ultrasound, IR). Preferably, data is collected by the sensors, which also observe the behaviour of the wearer, making it a two-way interaction between user and sensors. The sensors impact the feedback mechanisms (both visual and tactile) via the microcontroller that analyses the sensor input and converts it into an output. The output is preferably real-time with minimal delay, but input can also be stored for future analysis.

In a preferred embodiment, three pressure sensors 120 (121, 122 and 123) and three vibration motors 130 (131, 132, 133) are used. The sensors 120 and motors 130 are paired together and located at the heel (rear foot), toe (forefoot) and under the arch of the foot (mid foot). These pairs are linked individually—i.e. if only the toe of the wearer is on the ground, then only the motor in the toe area will vibrate. Likewise, if only the heel is on the ground, only the motor in the heel area will vibrate. This arrangement is beneficial as the vibrational feedback directly correlates to the contacting area. Other embodiments may include more or fewer sensors 120 and motors 130 and other pairings.

In the illustrated embodiments, the system is implemented as one or more attachments for footwear. In other embodiments, the system may be integrated within footwear.

The present invention may also be used to gather user data and correlate user data with the feedback. The present invention may further comprise an input device for receiving user data such as medical (disease and medication) history and biometric data. The present invention may further comprise storage to store this data and the sensor data, to identify trends in the data. The system may further comprise a wireless communications element to send and receive such data e.g. to a smartphone or smartwatch or directly to a computer or other storage facility, such as a memory card. In particular, the system may be operable to record pressure sensor data across the user's foot in real-time and store/transmit this data for real-time analysis of weight distribution, for example. The tactile feedback may be used to "train" the user to modify their weight distribution e.g. for improved performance, stability or strength as described above.

This data may be used to track disease progression (by the user, medical professional or in research), to link with medication that the user may be taking, as it may be that drug A is best for user A and drug B is best for user B, even if they are diagnosed with the same disease. Over time, it may also be possible to identify trends, that can be used for research purposes, to better understand the disease. The data may further help with diagnosis and in evaluation of clinical trials regarding new treatment and medication methods.

In the preferred embodiments, a vibration motor(s) where the force direction is vertical is used, as the human body is designed to absorb forces in a vertical direction. Vibration in a vertical direction may also increase circulation and lymphatic drainage, whilst improving proprioception, balance and posture.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

Preferred Features

1. Footwear or an attachment for footwear to assist a person walking in a direction of travel, e.g. a person with limited or impaired walking ability, comprising a device for projecting a line in front of the person wearing the footwear, the line either forming a path extending in the said direction of travel or a line extending across the direction of travel, e.g. at right angles to the direction of travel.

2. Footwear or an attachment for footwear as recited in clause 1, wherein the device is switchable between projecting a line forming a path extending in the said direction of travel and a line extending across the direction of travel.

3. Footwear or an attachment for footwear as recited in clause 1 or clause 2, wherein the device is capable of projecting a spot in front of the person wearing the footwear to assist in gauging the height of an obstacle lying along the direction of travel.

4. Footwear or an attachment for footwear as recited in any preceding clause, which comprises a pressure-sensor for detecting the pressure exerted by the person's foot on the ground, which sensor is capable of communication with the device to project a line only when the sensor detects a pressure above a predetermined threshold value.

5. Footwear or an attachment for footwear as recited in clause 4, wherein the device is configured to project a spot when the sensor detects a pressure below a threshold value.

6. Footwear or an attachment for footwear as recited in clause 4 or clause 5, which includes an insole and wherein the sensor is incorporated into the insole.

7. Footwear or an attachment for footwear as recited in clause 6, wherein the insole includes a vibrator capable of delivering a variable degree of vibration to the sole of the person's foot, which the sensor is capable of communication with the vibrator to provide a degree of vibration that increases with increasing pressure sensed by the sensor.

8. A method of assisting a person with walking in a direction of travel, e.g. a person with limited or impaired walking ability, which comprises projecting from the person's foot a line in front of the person, the line either forming a path extending in the said direction of travel or a line extending across the direction of travel, e.g. at right angles to the direction of travel.

9. A method as recited in clause 8, which compromises projecting a spot in front of the person wearing the footwear to assist in gauging the height of an obstacle.

10. A method as recited in any preceding clause 8 clause 9, which comprises sensing the pressure exerted by the person's foot on the ground, and projecting a line only when the sensor detects a pressure above a predetermined threshold value.

11. A method as recited in clause 10, which comprises projecting a spot when the pressure is below a threshold value.

12. A method as recited in clause 10 or clause 11, wherein a vibration is delivered to the sole of the person's foot and wherein the degree of vibration increases with increasing pressure sensed by the sensor.

13. A system for aiding a user to move, comprising:
 a sensor configured to detect a parameter indicating a position of the user's foot;
 a projector operable to project a first visual cue; and
 a processor, wherein the processor is configured to control the projector depending on the sensed parameter.

14. The system of clause 15, wherein the system is further operable to project a second visual cue, different to the first visual cue.

15. The system of clause 14, wherein:
 the first or second visual cue is a line projection indicating a path extending in a direction of intended travel; and/or
 the first or second visual cue is a dot projection.

16. The system of any of clauses 13 to 15, wherein the sensor comprises a pressure or distance sensor and the processor is configured to enable the first and/or second visual cue when the sensed pressure or distance is above a threshold value.

17. The system of any of clauses 13 to 15, wherein the sensor comprises a pressure or distance sensor and the processor is configured to enable the first and/or second visual cue when the sensed pressure or distance is below a threshold value.

18. The system of any of clauses 13 to 15, wherein the sensor comprises a pressure or distance sensor and the processor is configured to:
 enable the first or second visual cue when the sensed parameter is above a first threshold value; and
 enable the other of the first and the second visual cues when the sensed parameter is below a second threshold value.

19. The system of any of clauses 16 to 18, wherein the first and second threshold values are substantially the same.

20. The system of any preceding clause, wherein the system further comprises a motor, operable to provide vibrational feedback in response to the sensed parameter.

21. A system for aiding a user to move, comprising:
 a sensor configured to detect a parameter indicating a position of the user's foot;
 a motor operable to provide vibrational feedback in response to the sensor output; and
 a processor, wherein the processor is configured to control the vibrational feedback depending on the sensed parameter.

22. The system of clause 20 or 21, wherein the strength of the vibration is configured to increase as the sensed pressure increases or the sensed distance decreases.

23. The system of any preceding clause, wherein the position of the foot is either:
 in contact with a surface, or
 not in contact with a surface.

24. The system of any preceding clause, further comprising a wireless communications module for transmitting and/or receiving data.

25. The system of any preceding clause, in the form of footwear or an attachment for footwear.

26. The system of clause 12, in the form of footwear or an attachment for footwear, wherein:
 the sensor is a pressure sensor configured to detect a pressure exerted by the user's foot on a surface;
 the first visual cue is a line projection for indicating a path extending in a direction of intended travel;
 the system is operable to project a second visual cue in the form of a dot projection for highlighting obstacles; and
 the processor is configured to enable the first visual cue when the sensed pressure exceeds a threshold and to enable the second visual cue when the sensed pressure is below the threshold.

27. A method for aiding a user to move, comprising:
 measuring sensor data from a sensor configured to detect a position of the user's foot; and
 projecting a first visual cue indicating a direction of intended travel, depending on the sensed parameter.

28. The method of clause 27, wherein the method comprises:
 detecting when the user's foot is in contact with a surface; and
 projecting a first visual cue from a projector when the user's foot is in contact with the surface.

29. The method of clause 27 or 28, further comprising:
 projecting, from the user, a second visual cue, different to the first visual cue, for identifying obstacles;
 receiving and storing user data; and/or providing tactile feedback from a motor in response to the sensed pressure.

30. The method of any of clauses 27 to 29, wherein:
 the first or second visual cue is a line projection indicating a path extending in a direction of intended travel; and/or
 the first or second visual cue is a dot projection.

31. The method for aiding a user to walk of clause 27, wherein the sensor comprises a pressure sensor and the method involves:
    measuring sensor data from the pressure sensor; and
    projecting a first visual cue in the form of a line projection indicating a path extending in a direction of intended travel from a projector, when the sensed pressure is above a threshold value.

32. The method for aiding a user to walk of clause 27, wherein the sensor comprises a pressure sensor and the method involves:
    measuring sensor data from the pressure sensor;
    projecting a first visual cue in the form of a line projection indicating a path extending in a direction of intended travel from a projector when the sensed pressure is above a threshold value; and
    projecting a second visual cue in the form of a dot projection for highlighting obstacles when the sensed pressure is below the threshold value.

33. The method of any of clauses 27 to 32, wherein the sensor comprises one or more pressure sensors and the method comprises measuring the pressure values to determine the user's weight distribution.

34. A method for aiding a user to walk, comprising:
    measuring sensor data from a sensor configured to detect a position of the user's foot; and
    providing tactile feedback from a motor in response to the sensed parameter.

35. The method of clause 34, wherein the strength of the vibration is configured to increase as the sensed pressure increases or the sensed distance decreases.

The invention claimed is:

1. A system for aiding a user to move, comprising:
    a first sensor in the form of footwear or an attachment for footwear and configured to detect a first parameter indicating a position of the user's foot, wherein the first sensor is a pressure sensor configured to detect a pressure exerted by the user's foot on a surface;
    a second sensor, wherein the second sensor is a distance sensor configured to detect a distance parameter;
    a projector operable to project a first visual cue, the first visual cue is a line projection in the form of a line in front of the user, wherein the projector is configured to be rotated ninety degrees between a first orientation and a second orientation such that when the projector is in the first orientation the line is projected vertically in front of the user and when the projector is in the second orientation the line is projected horizontally in front of the user, wherein a processor of the system controls operation of the projector depending on the first parameter detected by the first sensor;
    wherein the projector is further operable to project a second visual cue in the form of a dot projection for highlighting obstacles;
    wherein the processor is configured to enable the first visual cue when the pressure detected by the first sensor exceeds a pressure threshold and to enable the second visual cue when the pressure detected by the first sensor is below the pressure threshold; and wherein the processor is further configured to enable at least one of the first and second visual cues when the distance detected by the distance sensor is below a distance threshold.

2. The system of claim 1, wherein the system further comprises a motor operable to provide vibrational feedback in response to the detected pressure.

3. The system of claim 1, further comprising a wireless communications module for transmitting and/or receiving data.

* * * * *